United States Patent [19]

Scala, Jr.

[11] 4,323,693
[45] Apr. 6, 1982

[54] BENZOIC ACID ESTER

[75] Inventor: Thomas L. Scala, Jr., West Milford, N.J.

[73] Assignee: Finetex, Inc., Elmwood Park, N.J.

[21] Appl. No.: 257,977

[22] Filed: Apr. 27, 1981

Related U.S. Application Data

[63] Continuation-in-part of Ser. No. 252,794, Apr. 13, 1981, which is a continuation-in-part of Ser. No. 74,071, Sep. 14, 1979, Pat. No. 4,275,222, which is a continuation-in-part of Ser. No. 949,630, Oct. 10, 1978, abandoned.

[51] Int. Cl.$^3$ .............................................. C07C 69/76
[52] U.S. Cl. ..................................... 560/103; 424/59; 424/60; 424/308
[58] Field of Search .................... 560/103; 424/59, 60, 424/308

[56] References Cited

U.S. PATENT DOCUMENTS 2,428,450 10/1947 Eitelman ............................. 560/103
3,506,704 4/1970 Miller ................................. 560/103

FOREIGN PATENT DOCUMENTS 130438 11/1946 Australia ............................. 560/103
1943453 10/1973 Fed. Rep. of Germany ...... 560/103

OTHER PUBLICATIONS

Chemical Abstract 39010r vol. 66, 1967.
Meyerson et al. JACS 95:18 Sep. 5, 1973 pp. 6056–6067.

Primary Examiner—Paul J. Killos
Attorney, Agent, or Firm—Weingram & Klauber

[57] ABSTRACT

A substantially pure benzoic acid ester of isostearyl ($C_{18}$) alcohol. The composition of this invention has unique properties in that it is non-greasy, has a low cloud point and pour point, is practically odorless, has low toxicity, and is stable. These properties make such composition useful as a vehicle or carrier, emollient or solubilizer for toiletry and cosmetic formulations, e.g., hair cream, hand cleaner, bath oil, suntan oil, brilliantine, anti-perspirants, perfumes and colognes, cold creams, electric pre-shave, eye and throat oil, fingernail polish, topical pharmaceutical ointments, lipsticks, stick rouge, skin lotions and creams, skin moisturizers, cleansing creams and after bath splash and lotions.

1 Claim, No Drawings

BENZOIC ACID ESTER

RELATED APPLICATIONS

This application is a continuation-in-part of co-pending application Ser. No. 252,794, filed Apr. 13, 1981, which is a continuation-in-part of Ser. No. 74,071 filed Sept. 14, 1979, now U.S. Pat. No. 4,275,222 which is a continuation-in-part of application Ser. No. 949,630 filed Oct. 10, 1978, now abandoned, all of which are entitled "Improved Ester Compositions".

Some of the novel uses of the claimed compositions in this application are described and claimed in concurrently filed U.S. Ser. No. 243,864, filed on Mar. 16, 1981, entitled "Skin Care Compositions" which is a continuation-in-part of U.S. Ser. No. 018,250 filed on Mar. 7, 1979 and entitled "Anti-Perspirant Composition" (now U.S. Pat. No. 4,278,655) which is a continuation-in-part of U.S. Ser. No. 100,917, filed Dec. 6, 1979, entitled "Fluid and Semi-Fluid Compositions including Benzoate Esters", (now U.S. Pat. No. 4,293,544). All of these aforementioned applications are assigned to the assignee of this application. The entire disclosures of all of these applications are incorporated herein by reference.

BACKGROUND OF INVENTION

1. Field of the Invention

This invention relates generally to a novel ester composition, and more particularly to a benzoic acid ester of isostearyl alcohol ($C_{18}$). The composition is particularly useful as a carrier and vehicle or an emollient and solubilizer for cosmetic and toiletry formulations.

2. Description of the Prior Art

Stearyl alcohol and isostearyl alcohol are well known alcohols each having the formula $C_{18}H_{38}O$. Commercially isostearyl alcohol is a mixture of branched methyl isomers with the general formula:

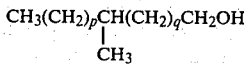

where p plus q is equal to 14.

A material of this type is available from Sherex Inc.

U.S. Pat. No. 3,506,704 to Miller et al describes a process for the production of organic esters produced in a liquid phase reaction of 1-hydrocarbyl bromides with hydrocarbonic acids. In the preferred embodiment of Miller et al, benzoic acid and n-dodecyl bromide ($C_{12}$) are reacted at an elevated temperature in the presence of lithium benzoate. Hydrogen bromide is evolved in the course of the reaction and attempts are made to remove the hydrogen bromide from the reaction zone. Miller et al states that such hydrogen bromide is well-known to cause extensive discoloration and deleterious effects.

In table III, Run 25 of Miller et al, benzoic acid is reacted with what is apparently a mixture of bromides in the $C_{11}$ to $C_{15}$ range. These mixtures are obtained from cracked wax alpha olefins which originate from petroleum, and thus are highly contaminated impure products. The Miller et al esters, as mentioned, are formed by a severe acid-bromide reaction and result in products which are invariably contaminated or discolored by hydrogen bromide. There is no disclosure in Miller et al of any benzoic acid ($C_{18}$) alcohol derivatives.

Further, certain linear alkyl benzoates are known in the art, e.g. lauryl benzoate, and stearyl benzoate. None of these benzoates have the unique properties of the ester composition described and claimed herein.

SUMMARY OF THE INVENTION

It is an object of this invention to provide a novel ester composition having unique properties which make it uniquely suitable as a vehicle or carrier in toiletry and cosmetic compositions.

It is a further object of this invention to provide a substantially pure benzoic acid ester of isostearyl ($C_{18}$) alcohol, said ester having unexpected properties not taught or suggested by the prior art, which make the composition uniquely suitable for broad application in toiletry and cosmetic compositions.

The foregoing objects and other objects are attained by a substantially pure benzoic acid ester of isostearyl ($C_{18}$) alcohol. This ester has the following structure:

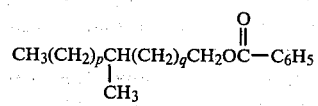

where p plus q equals 14.

DETAILED DESCRIPTION OF THE INVENTION

The compositions of this invention are produced by reacting benzoic acid with isostearyl alcohol. Preferably, methane sulfonic acid is used as a catalyst. It is contemplated, however, that any method of producing such benzoic acid ester can be utilized as long as such method does not interfere with the intended use, particularly in the cosmetic and toiletry field. In particular, the process for producing the esters should permit them to be purified to a substantially pure condition. By the use of the term "substantially pure," it is meant that the composition does not contain impurities which interfere with their intended use, particularly as carriers or vehicles in toiletry and cosmetic formulations. The composition may have, inter alia, minor amounts of esters of other alcohols which may have been mixed with the isostearyl alcohol.

It is believed that contributing to the uniqueness of the benzoic acid ester of this invention is the fact that the alcohol is specifically branched as indicated in the aforementioned representation. Comparative testing with n-stearyl alcohol (unbranched) and n-lauryl alcohol ($C_{14}$ unbranched) appears to indicate that branching is required in order to obtain an ester having the unique properties of the claimed composition.

The benzoic acid ester composition of this invention has unique properties particularly suited for use as a vehicle and a carrier in toiletry and cosmetic compositions.

The benzoic acid ester composition of this invention is characterized by the following properties:

1. Lack of greasiness;
2. Low cloud point and pour point;
3. Substantially no odor;
4. Low toxicity; and
5. Emulsifying properties.

The foregoing properties make the composition of this invention particularly useful in toiletry and cosmetic products, e.g., hair creams, hand cleaners, bath oils, suntan oils, hair brilliantines, antiperspirants, perfumes, colognes, sunscreen butters, cold creams, electric preshaves, eye and throat oils, skin gels, fingernail polishes, pharmaceutical ointments, deodorants, lotions, moisturizers, facial cleansers, and after bath splashes and lotions.

The following are non-limiting examples of processes for producing the composition of this invention, properties of the composition and uses of the composition in specific toiletry and cosmetic products.

BENZOIC ACID ESTER COMPOSITIONS

EXAMPLE 1

A mixture of 270 parts (1.0 mol) of the aforedescribed isostearyl alcohol, 122 parts (1.0 mol) of benzoic acid and 1.7 parts of methane sulfonic acid (as a catalyst) was stirred and heated under nitrogen to a temperature of 155° C. while collecting any distillate formed. When no more distillate came over and the acidity was less than 7 mg, it was cooled to 50° C. and washed. After washing again with a dilute salt solution, the ester layer was separated and heated under vacuum to remove traces of water. The benzoate ester composition was a clear liquid with practically no odor. The molecular weight was 374; specific gravity 0.929; and freezing point about $-35°$ C.

COMPARATIVE EXAMPLE 1

A mixture of 270 g. (1.0 mol) of the stearyl alcohol, 122 g. (1.0 mol) of benzoic acid and 1.7 g of methane sulfonic acid (as a catalyst) was heated under nitrogen with stirring to 155° C. and held at this temperature for hours until no more distillate was collected. The yield after washing and vacuum stripping was 346 g. (92.5%) of the solid benzoic acid ester of stearyl alcohol, i.e. an isomer of the composition of this invention. The benzoic acid ester of stearyl alcohol was a hard, wax-like solid, with a melting point of 37° C.

PROPERTIES OF AND USES FOR BENZOIC ACID ESTER COMPOSITION

EXAMPLE 2

Greasiness

A comparison of the composition of the present invention was undertaken with a benzoate ester of stearyl alcohol (Comparative Example 1).

It was found that the stearyl benzoate is a wax-like solid. When stearyl benzoate is rubbed between ones fingers, it has a greasy-waxy feel, and its presence on the skin was found to be still evident one-half hour after rub-in of same, whereas the isostearyl benzoate of this invention, although giving the feeling of emolliency, has a velvety feel which rapidly dissipated.

It may be noted that the foregoing result is deemed completely unexpected, since the isostearyl benzoate is a mere isomer of the stearyl benzoate.

EXAMPLE 3

Cloud Point and Pour Point

"Cloud point", refers to the temperature at which a waxy solid material appears as the liquid composition being examined is cooled. Cloud points are also associated with pour points, which is the lowest temperature at which a liquid will flow when a container is inverted.

In all cases as the temperature is lowered, the cloud point is detected first, with the pour point being generally 5°-25° F. lower.

It is an important characteristic of formulation development for toiletries and the like to utilize a product that has as low a cloud point as possible. This is a necessary requirement to prevent irreversible changes from occurring during the lifetime of a toiletry product exposed to varying ambient temperatures of, e.g., $-15°$ C. to 48° C.

Whereas stearyl benzoate has a cloud point determined at 37° C., the benzoic acid ester of isostearyl alcohol of the present invention, was found to have an astonishingly low cloud point of about $-10°$ C., and a pour point approaching $-33°$ C. This provides an enormous use and application advantage for the isotearyl benzoate. It broadens the application possibilities in personal care products, and gives handling ease.

EXAMPLE 4

Odor

Referring now to the characteristic of odor: Lack of odor is of enormous important in the development of consumer-oriented products. Many emollients have a characteristic odor that is obnoxious and in many cases difficult to mask. Where masking is possible, it is accomplished only at great expense.

Completely unexpectedly, it has been found that the composition of the present invention is for all practical purposes lacking in odor. A direct comparison was made, e.g., between the benzoic acid ester of isostearyl alcohol and stearyl benzoate—and yielded suprising results. Stearyl benzoate has a fatty odor, making it undesirable, e.g., as a fragrance diluent, whereas the product of the invention is near completely odorless.

The significance of this lack of odor may be appreciated (e.g., in fragrance applications) by observing that all formulas have a minimum fragrance level (MFL), at which the formula no longer has an inherent odor. However, even at this MFL the notes of the fragrance itself are not noticeable. A slight increase in fragrance level must be effected to be able to detect the fragrance oil. Thus, using the benzoic acid ester of isostearyl alcohol allows the use of lower fragrance levels, which in turn lowers costs for such applications—as compared to the use of stearyl benzoate.

EXAMPLE 5

Toxicity

Products of the type in which the present esters are incorporated, invariably come in contact with the consumer. Great care and caution are therefore exercised by manufacturers, and by state and federal agencies to insure the use of raw materials that are innocuous and free from harmful contaminants. Toxicity studies pertinent to the present compositions were accordingly conducted. It was unexpectedly found that for the benzoic acid ester of isostearyl alcohol, the results on acute oral toxicity (rate), $LD_{50}$, was greater than 5 g/kg of body weight. Industry normally considers a product having an $LD_{50}$ of greater than 5 g/kg as adequate. These results thus establish low toxicity. While precisely comparative data for stearyl benzoate is not available, the significance of the present finding may be appreciated by noting that the very commonly used ester, butyl benzoate has an $LD_{50}$ of 3.5 g/kg of body weight. Thus the product of the invention has a toxicity less than that of a commonly used, womewhat analogous product—which is unexpected.

EXAMPLE 6

Toxicity Comparison of Alcohol and Its Benzoate Ester

In the following Table I, the ester composition of the present invention is compared with the isostearyl alcohol with respect to toxicological studies. The composition of this invention is seen to be non-irritating to the eyes and non-irritating and non-sensitizing to the human skin. The $LD_{50}$ is quite high, showing the product of the invention to be remarkably safe if accidently ingested. By contrast, the irritation factors for isostearyl alcohol are significantly worse and indicate that a the alcohol is a "borderline" irritant.

TABLE I

| Characteristic Test | TOXICOLOGY | |
|---|---|---|
| | Isostearyl Alcohol | Isostearyl Benzoate of this Invention |
| Accute Oral Toxity (Rats $LD_{50}$) | >20 g/kg | >5 g/kg |
| Ocular Irritation (Rabbits), No wash | 6.0/24 hr 1.5/48 hr 0.3/72 hr | 1.2/24 hr. 0.0/thereafter |
| Primary Dermal Irritation Index (Rabbits) | 1.0/4.8 (two results) | 1.05 |

EXAMPLE 7

Stability

A most unusual and unexpected property of the benzoate ester of this invention is the remarkable chemical stability to hydrolysis over a pH range of approximately 2 to 12. To applicant's knowledge, all currently used ester compositions, i.e., compositions used in the type of applications for which the instant products find application, hydrolyze within this pH range, i.e., these prior art esters within at least a portion of the indicated pH range, will decompose by hydrolysis.

EXAMPLE 8

Bath Products

There are many types of bath products. The major ones are:
1. Bath salts
2. Floating bath oils
3. Dispersible bath oils
4. Emulsifiable bath oils
5. Soluble bath oils
6. Bath gels
7. Foaming bath oils
8. Aerosol bath oils
9. Specialty baths
10. Bubble baths All but bath salts and specialty baths contain oils as the major component. Many bath products contain oils as an additive.

The consumer seeks to overcome the drying effect upon the skin which results from soaking in a bath utilizing a soap or synthetic detergent for cleansing purposes. This dryness is due to oil removal from the skin by the detergent. Bath oils and emollient oils in detergent bath products impart emolliency and eliminate dryness to the skin. What is generally undesirable is the use of an emollient oil which is very oily or greasy as is the case with mineral oil.

There are 2 major problems with using an oil which imparts an oily feel to the skin; namely, the body feels excessively oily and slipping in the tub can lead to injury. Also, a bath tub ring is formed.

Oils properly formulated are deposited on the skin by the bath. The benzoic acid ester of this invention in a bath oil product is deposited on the skin and leaves a lubricating, velvety feel on the skin. Even in the presence of mineral oil, the ester will impart this same dry lubricating velvety feel to the skin. Should a more oily feel be desired, a large excess of mineral oil and a significant lower concentration of ester will produce this oily effect.

In addition to a dry lubricating feel to the skin, one other important property which the oil should possess is being toxicologically non-irritating and non-sensitizing. The benzoate ester is non-irritating and non-sensitizing to the skin. This conclusion is reached from tests on rabbits, guinea pigs, and humans. These properties, i.e., dry feel, non-irritation and non-sensitizing are unexpected. Isopropyl myristate, commonly used in bath products, has been suspect as an irritant.

Bath Oils

An example of a simple floating bath oil is as follows:

| FLOATING BATH OIL | |
|---|---|
| Benzoate ester of Isostearyl alcohol. | 95% |
| Pluronic L-92 (with ethoxylated (20%)/propoxylated (80%) nonionic) - (BASF-Wyandotte) | 1% |
| Fragrance | 4% |

An example of a simple dispersible bath oil is:

| DISPERSIBLE BATH OIL | |
|---|---|
| Benzoate ester of Isostearyl alcohol | 97% |
| Oleth - 10* | 3% |

*Ethoxylated (10 mole) oleyl alcohol.

Again, a dry lubricating feel is imparted to the skin. Another example of a dispersible bath oil is:

| DISPERSIBLE BATH OIL | |
|---|---|
| | % By Wt. |
| Benzoate ester of Isostearyl alcohol | 20.0 |
| Mineral Oil | 69.5 |
| Modulan[1] | 5.0 |
| PEG-400 Dilaurate | 5.0 |
| Fragrance, F1126 | 0.5 |

[1]Amerchol, a unit of CPC Int'l, Edison, N.J. 08902.

Procedure

Materials added in order listed and stirred.

Advantage

The benzoate ester reduces oiliness of mineral oil.

Here a significantly large amount of mineral oil is used with the ester in a ratio of 3.25:1. Surprisingly, a dry lubricating velvety feel is imparted to the skin. Another example of a dispersible bath oil is:

| "STAY CLEAR" BATH OIL | |
|---|---|
| | % by wt. |
| (A) Light mineral oil, N.F. | 45.00 |
| Benzoate ester/isostearyl alcohol | 25.00 |

-continued

"STAY CLEAR" BATH OIL

|     |     | % by wt. |
| --- | --- | --- |
|     | Lanolin oil | 2.50 |
|     | Fragrances (s) | 0.60 |
|     | PEG 400 dilaurate | 0.60 |
|     | PEG 200 DILAURATE | 3.60 |
| (B) | **Benzoate ester of isostearyl alcohol | 2.00 |
|     | D & C Violet #2 | 0.0002 |
|     | Antioxidant G-16[1] | 0.05 |
| (C) | PEG 200 DILAURATE | 0.08 |
|     | Uvinul M-40[2] | 0.005 |
| (D) | Light mineral oil, N.F. | 19.85 |

**If desired, prepare a stock solution and store in the dark for a later use.
[1]Griffith Laboratories, Inc., Jersey City, N.J. 07303
[2]GAF Corp., N.Y., N.Y. 10020

Procedure:
1. Combine and mix (A) in order listed.
2. Combine and mix (B) for 5 minutes and add to (A) with mixing.
3. Combine, mix and dissolve (C) and add to above and mix for 5 minutes.
4. Add (D) and mix total batch for about 25 minutes.

In this formulation, there is about 65% mineral oil plus 2.5% lanolin oil along with 25% ester. This is a quick blooming bath oil and there is no lanolin drop out. A dry lubricating velvety feel is imparted to the skin.

Many bubble bath or foaming bath oils do not contain an oil but are based on alkanolamide detergents. An example of a Bubble Bath Oil (or foaming bath oil) is shown below:

BUBBLE BATH OIL

|     |     | % by wt. |
| --- | --- | --- |
| (A) | TEA-Lauryl Sulfate, 40% | 40.0 |
|     | Disodium Monoricinoleamide MEA-Sulfosuccinate[2] | 1.5 |
|     | Linoleamide DEA[1] | 7.0 |
|     | Laneth-16 | 5.0 |
|     | Benzoate ester of isostearyl alcohol | 3.0 |
|     | PEG-7 Glycerol Cocoate[3] | 1.0 |
|     | Polysorbate 20 | 3.0 |
|     | Tetasodium EDTA | 0.1 |
| (B) | Water, purified | 36.5 |
| (C) | Water, purified | 2.0 |
|     | Quaternium-15[4] | 0.2 |
| (D) | Fragrance | 0.7 |
| (E) | Color | q.s. |

[1]Aminol LNO (FINETEX)
[2]Rewoderm S-1333 (Rewo, Div. Emery Ind.)
[3]Standamul HE (Henkel)
[4]Dowicil 200 (Dow Chemical Co.)

Procedure:
1. Combine and mix (A). Heat and mix to 75° C.
2. Heat (B) to 76°-78° C. Add to (A).
3. Mix and cool to 41°-43° C.
4. Mix (C) and add to above mix.
5. Add (D) and (E); mix and cool to 20°-24° C.

Advantage:
A true bubble bath oil with long lasting bubbles and a luxurious after feel.

A problem of bubble bath is the defatting of skin by the detergents. As little as 3% ester provided a dry emollient after-feel while not significantly altering the foaming properties of the detergents. Esters are known to appreciably affect the foaming properties of detergents and are considered foam suppressants. This was another unexpected property of the esters.

Bath Gelee Sachet

An example of a soap bar or soap/syndet bar or syndet bar containing an emollient oil.

Toilet soap bars were prepared in commercial soap equipment containing essentially:

| Soap | 97.5% |
| --- | --- |
| Benzoate ester of isostearyl alcohol | 2.0% |
| Fragrance | 0.5% |
| Color | q.s. |

Upon washing, rinsing, and drying, a slight dry emollient feel was discovered. Larger concentrations of esters improve the degree of dry emolliency. The imparted emolliency is desired by consumers since soap is defatting to the skin.

Bath Oil

In this Example, a satinized, protein bath oil was prepared using the benzoate ester as the emollient carrier. More specifically, four sub-mixtures A, B, C, D, were initially prepared which included individual components as follows:

|     | Component | % by Weight |
| --- | --- | --- |
| A.  | light mineral oil, N.F.** | 42.00 |
|     | benzoate ester* | 23.00 |
|     | lanolin oil** | 2.50 |
|     | fragrances | 0.60 |
|     | PEG-8 dilaurate** | 0.60 |
|     | Lexein A440[1] | 5.00 |
|     | PEG-4 dilaurate** | 3.60 |
| B.  | benzoate ester* | 2.00 |
|     | D & C Violet #2** | 0.0002 |
|     | D & C Green #6** | 0.0001 |
|     | antioxidant | 0.05 |
| C.  | PEG-4 dilaurate** | 0.80 |
|     | benzophenone-4** | 0.005 |
| D.  | light mineral oil | 19.85 |

[1]Myristyl hydrolyzed animal protein product of Inolex Corp., Chicago, Illinois 60609
*The benzoate ester utilized in this Example was the benzoic acid esters of isostearyl alcohol.
**Identification is in accordance with the CTFA Cosmetic Ingredient Dictionary, 2nd Ed., 1977. (Published by The Cosmetic Toiletry, and Fragrance Association, Inc., 1135 15th St., NW, Washington, D.C. 20005). Unless otherwise indicated, all name designations in the Examples of this specification shall have the same CTFA reference.

The procedure used in preparing the bath oil of this Example involved an initial combination of the components of sub-mixture A in the order listed therein. The combined components of sub-mixture B were mixed for five minutes and then added to sub-mixture A with additional mixing. The compounds of sub-mixture C was combined, mixed and dissolved, and then added to A and B, with further mixing for five minutes. Finally, the light mineral oil, i.e., sub-mixture D was added; and the total batch mixed for about 25 minutes. The resultant product is essentially an anhydrous solution in which the benzoate ester is a vehicle with the mineral oil. When applied to the skin, it was found to provide a very satiny feel. The moisture-laden protein is effectively locked to the skin by use of the said composition, to produce a soft, comfortable feeling at the skin surface. The product was found to yield a "dry hand", i.e., while acting as a excellent emollient, it nonetheless produced a smooth, non-oily feel upon the skin surface. This was especially suprising in view of the very high quantities of mineral and other oils present in the composition.

EXAMPLE 9

Proteinized Suntan Oil

In this Example, a "proteinized suntan oil" was prepared using the compositions of this invention. The components of the composition were as follows:

| Component | % By Weight |
| --- | --- |
| S.D. alcohol | 85.00 |
| Benzoate ester* as vehicle | 5.00 |
| PEG-8 | 0.25 |
| Hydroxpropyl cellulose | 0.75 |
| Mink amido propyl dimethyl 2-hydroxyethyl ammonium chloride | 0.60 |
| Hydrolyzed animal protein | 5.00 |
| Octyl dimethyl PABA | 3.25 |
| Fragrance | 0.15 |

*benzoic acid ester of isostearyl alcohol.

The alcohol was combined with the PEG-8 and mixed rapidly with addition of the hydroxyethyl cellulose. The resultant product was mixed for 45 minutes and the benzoate ester was then added. The remainder of the components were then added in the order listed, and further mixing was employed. The resultant final product was found to be water-resistant and tack-free on application. Although having a non-greasy feel, it yet displayed excellent emollient properties and prevented drying of the skin.

EXAMPLE 10

Sunscreen Butter

In this Example, a "sunscreen butter" was prepared using the compositions of this invention. The following components were combined and mixed in the formulation:

| Component | % by Weight |
| --- | --- |
| Isostearyl benzote | 64.0 |
| NEODOL 25 alcohol | 18.5 |
| Glyceryl C$_{18-36}$ wax acid ester | 8.0 |
| Lanolin oil | 6.0 |
| Lanolin alcohol | 1.0 |
| Ethyl dihydroxpropyl PABA | 1.5 |
| Steartrimonium hydrolyzed animal protein | 0.5 |
| Fragrance | 0.5 |

The resultant composition was, again, a non-greasy feeling, dry, lubricating cream composition with excellent spreading characteristics.

EXAMPLE 11

Cold Cream Cleanser

In this Example, a cold cream cleanser was prepared using the compositions of this invention. The components of the composition were as follows:

| | Component | % by Weight |
| --- | --- | --- |
| A. | water | 53.60 |
| | propylene glycol | 4.00 |
| | magnesium aluminum stearate | 1.50 |
| B. | glyceryl stearate, S.E. | 7.50 |
| | mineral oil, light, N.F. | 14.80 |
| | benzoate esters* as vehicle | 9.00 |
| | lanolin oil | 0.50 |
| | mineral oil (and) lanolin alcohol | 2.50 |
| | cocyl sarcosine | 0.50 |
| | methyl paraben | 0.10 |
| | antioxidant | 0.50 |
| C. | water | 1.00 |
| | quaternium-15 | 0.10 |
| D. | fragrance | 0.50 |

*Benzoic acid ester of Isostearyl alcohol.

In preparing the composition, the components of group A were mixed rapidly for 25 minutes then heated to 70° C. The components of group B were then mixed and heated to 70° C. Group B was then added to group A while stirring. With continued stirring, the mix was cooled to 40° C. The components of group C were mixed and added; further stirring was used, and the fragrance (D) was added. The composition was cooled to 25° C. to yield the final product.

The resultant product was an easily spreadable, effective cleansing cream. When applied to the skin, it left same soft and moisturized. Particularly to be noted was that the said product imparted a velvety, non-greasy lubricating feel—even (as here) in the presence of substantial quantities of mineral oil.

EXAMPLE 12

Electric Preshave

In this Example, a so-called "electric preshave" lotion was prepared using the ester composition of this invention. The composition included components as follows:

| | Component | % by Weight |
| --- | --- | --- |
| 1. | S.D. alcohol | 85.8 |
| 2. | Cyclomethicone** | 10.0 |
| 3. | Benzoate esters* | 4.0 |
| 4. | Phenyl dimethicone | 0.1 |
| 5. | Fragrance | 0.1 |
| 6. | Color | q.s. |

*Benzoic acid ester of Isostearyl alcohol.
**CTFA designation for volatile silicone In preparing the composition, components 2, 3, 4, and 5, were mixed and blended; component 6 is added, followed by thorough mixing; thereupon component 1 is added and further thorough mixing applied. The resulting product was a clear fluid which was easily and quickly applied to the face prior to shaving. It dried excess facial moisture and provided excellent lubrication to the face and electric shaver, to aid in providing a close, painless shave. Especially noteworthy was the dry, velvety feel provided by the composition when applied to the skin. This is sharply contrasted with the oily feel which is present when a generally similar composition is used, which employs conventional IPM as a vehicle.

EXAMPLE 13

Eye And Throat Oil

In this Example, an eye and throat oil was prepared in accordance with the invention. The composition included components as follows:

| | Component | % by Weight |
| --- | --- | --- |
| 1. | benzoate esters* | 46.30 |

-continued

| Component | | % by Weight |
|---|---|---|
| 2. | lanolin oil | 7.70 |
| 3. | isopropyl lanolate & lanolin oil | 1.00 |
| 4. | mineral oil, light, N.F. | 44.80 |
| 5. | BHA | 0.05 |
| 6. | propyl paraben | 0.05 |
| 7. | fragrance | 0.10 |

*Benzoic acid ester of Isostearyl alcohol.

In preparing the composition, components 1 through 5 were combined and mixed. Component 6 was added and the blend mixed to dissolve. As necessary, the blend was warmed to 48°–50° C. Component 7 was added and the composition mixed for 15 minutes. The final resultant product was a quickly absorbed oil that left the skin with a velvet smooth film. The product had a non-greasy, lubricating and velvety feel, even in the presence of very high amounts of mineral and other oils.

EXAMPLE 14

Skin Gel

In this Example, a "skin gel" was prepared using the ester composition of this invention. The composition included components as follows:

| Component | % by Weight |
|---|---|
| Glyceryl tribehenate soap | 7.5 |
| Benzoate esters* | 90.5 |
| Fragrance, color, preservative | q.s. |

*Benzoate acid ester of Isostearyl alcohol.

In preparing the composition, the first two components were combined, mixed and heated to 110°–115° C. Mixng was continued and the blend cooled to 40°–45° C. The fragrance was added and mixed, and the blend cooled to 25°–27° C. to yield the final product. Such product was found to be a smooth, emollient, grease-less-feeling skin gel, which was quickly absorbed by the skin, leaving a pleasant velvety afterfeel.

EXAMPLE 15

Fingernail Polish

In this Example, a fingernail polish remover/conditioner was prepared using the composition of this invention. The composition included components as follows:

| | Content | % by Weight |
|---|---|---|
| A. | ethyl acetate | 15.00 |
| | acetone | 74.00 |
| | Albinco Gel "B"** | 1.00 |
| B. | protein fatty acid condensate | 1.10 |
| | acetylated lanolin alcohol | 1.00 |
| | benzoate esters* | 3.00 |
| | water | 4.00 |

**Carbohydrate based mixed ester-ether gum product of Anheuser-Busch, Inc., St. Louis, Missouri
*Benzoic acid ester of Isostearyl alcohol.

In preparing the composition, the ethylacetate and acetone were combined, the Abinco Gel "B" added, and the blend was mixed well for about 40 minutes, to swell the gum. While mixing, the components of group B were added in the order listed. The blend was thereupon mixed for 10 minutes to yield the final product. Such product, when utilized, prevented "whitening" and dryness of the fingers and skin, and provided dry lubrication and a good cosmetic feel and emolliency to the fingers.

EXAMPLE 16

Hair Brilliantine

In this Example, a hair "brilliantine" was prepared using the ester composition of this invention. The composition included components as follows:

| Component | % by Weight |
|---|---|
| Acetulan** | 5.0 |
| Benzoate ester* | 94.5 |
| Fragrance | 0.5 |
| Preservative, color | q.s. |

**Acetylated lanolin alcohol product of Amerchol, Div. of CPC International, Edison, New Jersey 08817
*Benzoic acid ester of Isostearyl alcohol.

In preparing the composition, the several components were combined and mixed in the order listed. The resultant product was a non-greasy, easily applied brilliantine, which increased hair gloss and provided a healthy appearance for same, while also making the hair manageable.

Topical Pharmaceutical Ointment

EXAMPLE 17

A. In this Example, a hydrophilic ointment base was prepared—i.e., an oil-in-water emulsion—using the ester compositions of this invention. The base was typical of those used in topical pharmaceutical ointments and included components as follows:

| | Component | % by Weight |
|---|---|---|
| A. | stearyl alcohol | 5.00 |
| | cetyl alcohol | 5.00 |
| | glyceryl stearate, S.E. | 3.00 |
| | mineral oil | 3.00 |
| | benzoate ester* | 5.00 |
| | antioxidant | 0.10 |
| | Sorbitan oleate emulsifier | 2.00 |
| B. | water | 70.33 |
| | propylene glycol | 4.00 |
| | methyl paraben | 0.17 |
| | propyl paraben | 0.05 |
| | PEG-40 stearate | 0.75 |
| | Sta-Sol** | 0.85 |
| C. | Polysorbate 60 | 0.50 |
| | fragrance | 0.25 |

**Lecithin product of A. E. Staley Mfg. Co., Decatur, Illinois, 62525
*Benzoic acid ester of Isostearyl alcohol.

In preparing the composition, the components of group A and the components of group B were separately mixed and heated to 65° C. With stirring, group A was then added to group B and mixed for 15 minutes. The blend was cooled to 35° C. and the group C components were added. The resultant product was a smooth spreading ointment base, which when applied to the skin provided a pleasant emolliency, yet without a greasy feel.

EXAMPLE 18

In this Example a lipophilic ointment base was prepared—i.e. a water-in-oil emulsion—using the ester composition of this invention. The base was again typical of those used in topical pharmaceutical ointments, and included components as follows:

|   | Component | % by wt. |
|---|---|---|
| A. | benzoate esters* | 5.0 |
|   | oleth-2 emulsifier | 5.0 |
|   | propyl paraben | 0.1 |
| B. | methyl paraben | 0.1 |
|   | sorbitol | 5.0 |
|   | water | 84.8 |

*benzoic acid ester of Isostearyl alcohol.

In preparing the composition, the components of group A and the components of group B were separately combined and mixed. With stirring, group B was then slowly added to group A—with the stirring rate being increased as the emulsion thickened. The resultant product was again found to be a smooth spreading ointment base, which when applied to the skin provided a pleasant emolliency, without any greasy feel.

EXAMPLE 19

Cold Cream

To demonstrate the desired dry lubricating properties of the benzoic acid ester composition of this invention, a basic cold cream was prepared utilizing 40% mineral oil in one formulation (FORMULATION A) and 20% mineral oil and 20% of the isostearyl benzoate (FORMULATION B). These formulations are listed below:

BASIC COLD CREAM COMPARISON

|   |   | % by wt. | |
|---|---|---|---|
|   |   | FORMULATION A | FORMULATION B |
| A. | Water, purified | 43.20 | 43.20 |
|   | Veegum (Magnesium Aluminum Silicate)* | 1.00 | 1.00 |
|   | Borax (Sodium Borate) | 0.50 | 0.50 |
|   | Methyl paraben (methyl p-hydroxbenzoate) | 0.20 | 0.20 |
| B. | Light mineral oil, N.F. | 40.00 | 20.00 |
|   | Beeswax, white, U.S.P. | 10.00 | 10.00 |
|   | Paraffin wax, 133-135° F. | 5.00 | 5.00 |
|   | Isstearyl benzoate | — | 20.00 |
| C. | Fragrance | 0.10 | 0.10 |
|   |   | 100.00 | 100.00 |

Procedure
1. Rapidly stir water and slowly add Veegum. Stir for 20 minutes then heat to 83°-85° C. while mixing.
2. Add Borax and Methyl paraben and stir.
3. Mix and heat B to 80°-82° C.
4. While B is being mixed, add A.
5. Q.S. with water if necessary.
6. Mix rapidly while cooling to 41°-43° C.
7. Add fragrance, C; mix and cool to 24°-27° C.

A panel was given each formulation to apply to his or her skin and to describe the difference, if any, on the feel on the skin.

The panel selected FORMULATION B as giving a "lighter" feel with good emolliency and FORMULATION A as being "heavy."

The use of the benzoic acid ester of this invention gives a cream with a softer consistency which yields a lighter feel when the cold cream is applied to the skin and leaves the skin feeling smooth. Additionally, the ester gives a higher gloss to the cold cream.

EXAMPLE 20

Cold Cream Cleanser-Conditioner

|   |   | % by wt. |
|---|---|---|
| A. | Water, purified | 53.63 |
|   | Propylene glycol | 4.00 |
|   | Veegum (Magnesium Aluminum Silicate)[1] | 1.50 |
| B. | Cerasynt Q (Glyceryl Stearate, self-emulsifying)[2] | 10.00 |
|   | Pluronic F-68 (Poloxamer 188, a block polymer)[3] | 3.00 |
|   | Mineral Oil, Light N.F. | 14.00 |
|   | Isostearyl benzoate | 9.00 |
|   | Lanolin Oil | 0.50 |
|   | Amerchol L-101 (Mineral oil + lanolin alcohol)[4] | 2.50 |
|   | Hamposyl C (Cocoyl sarcosinate)[5] | 0.50 |
|   | Methyl paraben (Methyl p-hydroxybenzoate) | 0.15 |
|   | Antioxidant G-50[6] | 0.05 |
| C. | Water | 1.00 |
|   | Dowicil 200 (Quaternium 15)[7] | 0.12 |
| D. | Fragrance | 0.05 |
|   |   | 100.00 |

[1]R. T. Vanderbilt Co., Norwalk, CT 07855
[2]Van Dyk & Co., Belleville, NJ 07109
[3]BASF Wyandotte Corporation, Wyandotte, MI 48902
[4]Amerchol, a unit of CPC Int'l, Edison, NJ 08817
[5]Organic Chemicals div., W. R. Grace & Co., Nashua, NH 03061
[6]Griffith Laboratories, Union City, NJ 07083
[7]Dow Chemical Co., Midland, MI 48640

Procedure
1. Mix A rapidly for 25 minutes and then heat to 71°-73° C.
2. Mix and heat B to 69°-71° C. and add B to A.
3. Continue to mix and cool to 41°-43° C. Combine C and add to cream.
4. Add D. Mix and cool to 20°-23° C.

A light modern cream, balanced for cleansing and emolliency without greasy residue. Wipe on/off; wipe on/wash off, or wipe on/leave on to soften skin and simplify makeup removal.

EXAMPLE 21

Light Cold Cream

|   |   | % by wt. |
|---|---|---|
| A. | Isostearyl benzoate | 10.00 |
|   | Antioxidant G-50[1] | 0.10 |
|   | Mineral Oil, light N.F. | 10.00 |
|   | Cerasynt 945 (Glycerol monostearate)[2] | 7.00 |
|   | Sorbotex AA (Mineral oil, lanolin alcohol, and glyceryl oleate)[2] | 2.00 |
|   | Tween 60 (Polysorbate 60)[3] | 0.50 |
|   | Propyl paraben (Propyl p-hydroybenzoate) | 0.10 |
|   | Cetyl alcohol | 6.30 |
| B. | Water, purified | 55.70 |
|   | Glycerin | 8.00 |
|   | Glydant, DMDM Hydantoin, 55% Solution[4] | 0.15 |
| C. | Fragrance | 0.15 |

[1]Griffith Laboratories, Union City, NJ 07083
[2]VanDyk & Co., Inc., Belleville, NJ 07109
[3]ICI Americas, Inc., Wilmington, DE 19899
[4]Glycol-Chemicals, Inc., Greenwich, CT 06830

Procedure
1. Mix and heat ingredients A to 61°-63° C.
2. Add to previously mixed ingredients B, mix and heat to 63°-65°.
3. Mix and cool to 41°-43° C. Add fragrance.
4. Mix and cool to R.T.
5. Twelve to fourteen hours after batch is completed, remix for maximum of physical appearance.

This cream has a smooth dry velvety feel with improved spreadability.

EXAMPLE 22

Hand Lotion

| | % by wt. |
|---|---|
| A. Isostearyl benzoate | 12.00 |
| Unimulse C (Dairy solids co-dried with nonionic and anionic emulsifiers)[1] | 2.00 |
| Steralchol (Mineral oil and lanolin alcohol)[2] | 3.00 |
| Fragrance | 0.50 |
| B. Water, purified | 76.50 |
| Dowicil 200 (Quaternium-15)[3] | 0.20 |
| Tetrasodium Edetate | 0.20 |
| C. Propylene Glycol | 3.30 |
| Ajidew N-50 (Sodium pyrrolidone carboxylate)[4] | 2.00 |
| Methyl Paraben (methyl p-hydroxybenzoate) | 0.20 |
| Propyl Paraben (propyl p-hydroxybenzoate) | 0.10 |

[1]Synfleur-Fidco Co., Monticello, NY 12701
[2]The Lanaetex Products., Inc., Elizabeth, NJ 07206
[3]Dow Chemical Co., Midland, MI 48640
[4]Ajinmoto Company of New York, Inc., New York, NY 10022

Procedure
1. Combine and mix Phase A.
2. Combine and mix Phase B.
3. Stirring, gradually add Phase B to Phase A.
4. Combine and mix Phase C and add Phase C to A & B with high-speed stirring for three to five minutes.

A cold processed oil-in-water lotion containing a milk derived protein and the sodium salt of a natural occurring skin humectant. It also conditions and acts as a moisture trap. The benzoate esters of this invention provide emolliency without an oily feel and ease of emulsification without heating.

EXAMPLE 23

Skin Moisturizer

| | | % by wt. |
|---|---|---|
| A. | Water, purified | 86.10 |
| | Glycerin | 2.00 |
| | Methylparaben | 0.15 |
| | PEG-40 stearate[1] | 0.50 |
| B. | Isostearyl benzoate* | 4.00 |
| | Glycerol stearate SE[2] | 2.50 |
| | Cetyl Alcohol | 3.50 |
| | Dimethicone[3] | 1.00 |
| | Propylparaben | 0.50 |
| C. | D & C Green #5, 1% Aq. soln. | 0.10 |
| D. | Fragrance | 0.10 |

[1]Myrj 52S (ICI Americas)
[2]Cerasynt Q (Van Dyk & Co.)
[3]Silicone Fluid SF-96 (General Electric/Silicones)

Procedure
1. Mix and heat A to 65°-67° C.
2. Mix and heat B to 63°-65° C.
3. Add B to A with mixing.
4. Cool to 45° C. with mixing. Add color C.
5. Cool to 40°-43° C. with mixing. Add fragrance D.
6. Mix and cool to 23°-26° C.

This formulation demonstrates a dry velvety feel. A similar formulation without the benzoate, is oil and greasy. When isopropyl myristate is substituted for the benzoate, the product is still oily.

EXAMPLE 24

Light Body Lotion

| | % by wt. |
|---|---|
| A. Isostearyl benzoate | 5.00 |

| | % by wt. |
|---|---|
| Amerchol L-101 (Mineral oil + lanolin alcohol)[1] | 4.00 |
| Stearic acid | 2.40 |
| Cerasynt Q (Glyceryl Stearate, self-emulsifying)[2] | 2.00 |
| Sesame Oil | 4.40 |
| Antioxidant G-50[3] | 0.15 |
| Propyl paraben (propyl p-hydroxybenzoate) | 0.05 |
| B. Water, purified | 74.95 |
| Glycerin | 4.50 |
| TEA, 85% (Triethanolamine) | 1.10 |
| Methyl paraben (methyl p-hydroxybenzoate) | 0.15 |
| C. Fragrance(s) | 0.25 |
| D. D & C Yellow #10, 0.5% aq. soln. | 0.05 |

[1]Amerchol, a unit of CPC Int'l., Inc., Edison, NJ 08817
[2]Van Dyk & Co., Belleville, NJ 07109
[3]Griffith Laboratories, Union City, NJ 07083

Procedure
1. Mix ingredients A and heat to 55° C.
2. Mix B with no heat.
3. Add A to B, mix and heat to 60° C.
4. Mix and cool to below 27° C.

The benzoate eliminates the oil feel of mineral oil and oil and improves spreadability.

EXAMPLE 25

Facial Cleanser Emulsion

| | % by wt. |
|---|---|
| A. Cerasynt MN (Glycol Stearate SE)[1] | 0.50 |
| Cetyl alcohol | 0.20 |
| Steary alcohol XXX | 0.20 |
| Isostearyl benzoate | 0.60 |
| PEG 400 diisostearate | 3.50 |
| B. Hamposyl L-30 (Sodium Lauroyl Sarcosinate)[2] | 10.00 |
| C. AMINOL LM-5C | 7.00 |
| D. Methyl paraben | 0.20 |
| Propyl paraben | 0.05 |
| Propylene glycol | 9.00 |
| E. Lactic acid, 85% | 1.20 |
| F. Water, purified | 67.50 |
| Disodium EDTA | 0.02 |
| G. FD&C Green (1% aq. soln.) | 0.03 |
| (ph = 4.7-5.1) | |

[2]Van Dyk & Co., Belleville, NJ 07109
[3]Hampshire Chemical Div., W. R. Grace & Co., Nashua, NH 03060

Procedure
1. Mix and warm A ingredients to 65° C.
2. Add B to A with agitation at 65° C.
3. Add C to above and agitate at 65° C.
4. Mix D to dissolve with slight heat. Add to above mix.
5. Add E to above with agitation. May be diluted with water from F.
6. Mix F and heat to 60° C. Add step 5 mix to the water (F) mix. Agitate and cool to 45° C.
7. Add G above at 45° C. Mix and cool to R.T.

This formulation demonstrates that even at a low concentration of benzoate in the formulation, the benzoate imparts a dry emollient feel to the skin while enhancing the solubility of facial oils.

EXAMPLE 26

Improved Water-In-Oil Cleansing Cream

| | % by wt. |
|---|---|
| A. Beeswax, white | 11.00 |
| Cetyl alcohol | 2.50 |
| Cetyl palmitate | 2.20 |

-continued

|  | % by wt. |
|---|---|
| Mineral oil, light, NF | 28.00 |
| Isostearyl benzoate | 20.60 |
| Cerasynt Q (Glyceryl stearate, self-emulsifying)[1] | 0.75 |
| Propyl paraben (propyl p-hydroxybenzoate) | 0.05 |
| B. Water, purified | 32.83 |
| Borax (sodium borate) | 0.75 |
| Methyl paraben (methyl p-hydroxybenzoate) | 0.15 |
| C. Water, purified | 1.00 |
| Dowicil 200 (Quaternium-15)[2] | 0.10 |
| D. Fragrance | 0.07 |

[1] Van Dyk & Company, Inc., Belleville, NJ 07109
[2] Dow Chemical Co., Midland, MI 48640

Procedure
1. Mix and heat A to 81°–83° C.
2. Mix and heat B to 83°–85° C.
3. Add B to A and mix rapidly. Cool to 55° C.
4. Dissolve C and add to cream.
5. Cool to 40°–42° C. before adding D. May be homogenized at this point.
6. Continue mixing and cool to 24°–28° C.

The benzoate of this invention improve cleansing action while eliminating the greasy feel of the high content of mineral oil. Provide for easy wipe on/off action and dry emolliency. Can be used as a night cream.

EXAMPLE 27

After Bath Splash

|  |  | % by wt. |
|---|---|---|
| A. | S.D. alcohol 39C, 190° proof ethanol | 90.25 |
| B. | Isostearyl benzoate | 5.75 |
| C. | Procetyl AWS (PPG-5-Ceteth-20)[1] | 1.30 |
| D. | Glycerin, USP | 1.50 |
| E. | Standamul G-16 (Isocetyl alcohol)[2] | 0.90 |
| F. | Fragrance | 0.30 |

[1] Croda, Incorporated, New York, NY 10010
[2] Henkel, Inc., Fort Lee, NJ 07024

PROCEDURE:
1. Mix ingredients in order listed.
2. Agitate batch for about 25 minutes.

A refreshing astringent, non-oiling emollient for application to damp-dry skin, after bath or shower. The benzoate provides for non-oily emolliency in the presence of a high amount of ethanol, generally considered to be drying to the skin.

EXAMPLE 38

After Bath Lemon Body Lotions

|  |  | % by Weight |
|---|---|---|
| A. | Water, purified | 69.25 |
|  | Carbopol 941 (Carboxy vinyl polymer)[1] | 0.30 |
| B. | Dry Flo (Aluminum Starch Octenylsuccinate)[2] | — |
|  | Ster-O-Pro (Oat Powder)[3] | 4.20 |
| C. | Isostearyl benzoate | 4.00 |
|  | Solulan 98 (Acetylated ethoxylated lanolin)[4] | 1.00 |
|  | Alcolec 4135 (lecithin)[5] | 0.50 |
|  | Propyl paraben (propyl p-hydroxybenzoate) | 0.05 |
|  | Methyl paraben (methyl p-hydroxybenzoate | 0.15 |
| D. | SD 40/190° Alcohol | 20.00 |
|  | TEA, 85% (Triethanolamine) | 0.30 |
| E. | D & C Yellow #5, 0.5% aq. sol | 0.05 |
|  | D & C Yellow #10, 0.5% aq. sol | 0.05 |
| F. | Shaw Mudge Lemon #M5405 | 0.05 |
|  | Perry Bros. Lemon-Musk #72-271 | 0.10 |

[1] B.F. Goodrich Chemical Div., Cleveland, OH 44131
[2] National Starch & Chemical Co., Bridgewater, NJ 08807
[3] Quaker Oats Co., Chicago, IL 60654
[4] Amerchol, a unit of CPC Int'l, Inc., Edison, NJ 08817
[5] American Lecithin Co., Woodside, NY 11377

PROCEDURE:
1. Thoroughly disperse Carbopol 941 in water.
2. Add Dry Flo or Ster-O-Pro and mix 25 minutes.
3. Mix TEA in ethanal and add to above; mix for 5 minutes.
4. Combine and mix C and add to above; mix
5. Add color and fragrance and mix for 15 minutes.

A light astringent and emollient hydroalcoholic lotion with a clean, velvety after-feel. An example of a hydroalcohol lotion with a low concentration of benzoate imparting a velvety after-feel.

While the present invention has been particularly set forth in terms of specific embodiments thereof, it will be understood in view of the present disclosure, that numerous variations upon the invention are now enabled to those skilled in the art, which variations reside within the scope of the present teaching. Accordingly, the invention is to be broadly construed, and limited only by the scope and spirit of the claims now appended hereto.

What is claimed is:
1. A benzoic acid ester of isostearyl alcohol.

* * * * *